United States Patent

Vandagriff et al.

[11] Patent Number: 5,241,189
[45] Date of Patent: Aug. 31, 1993

[54] INK CONCENTRATION SENSOR FOR MAINTAINING DYE CONCENTRATION IN AN INK JET PRINTER

[75] Inventors: Randy D. Vandagriff, Dayton; Robert J. Simon, West Carrolton; Randal L. Mullins, Jamestown; Russell L. Bartley, Urbana, all of Ohio

[73] Assignee: Eastman Kodak Company, Rochester, N.Y.

[21] Appl. No.: 891,332

[22] Filed: May 29, 1992

[51] Int. Cl.$^5$ ............................................. G01N 21/40
[52] U.S. Cl. ................................... 250/575; 356/435; 346/140 R
[58] Field of Search ........................ 250/575, 573, 205; 346/1.1, 75, 140 R; 356/435, 436, 442

[56] References Cited

U.S. PATENT DOCUMENTS

| | | | |
|---|---|---|---|
| 3,900,396 | 8/1975 | Lamadrid | 250/575 |
| 4,609,991 | 9/1986 | Minton et al. | 356/436 |
| 4,884,065 | 11/1989 | Crouse et al. | 250/573 |

Primary Examiner—David C. Nelms
Assistant Examiner—Que T. Le
Attorney, Agent, or Firm—Thomas H. Close

[57] ABSTRACT

An ink concentration sensor maintains ink concentration in an ink jet printing system. The ink concentration sensor includes a transparent fluid chamber and an infrared light source for directing a beam of IR light at the fluid chamber. A first sensor is located for receiving IR light reflected from the surface of the chamber and providing a reference signal and a second sensor is located for receiving IR light transmitted through the chamber to produce a concentration signal. A circuit receives the reference signal and generates a corrected concentration signal.

10 Claims, 2 Drawing Sheets

INK CONCENTRATION SENSOR FOR MAINTAINING DYE CONCENTRATION IN AN INK JET PRINTER

TECHNICAL FIELD

The present invention relates to continuous ink jet printers and, more particularly, to measurement of ink concentration for control in a continuous ink jet fluid system.

BACKGROUND ART

Ink concentration of an ink cell, used in optical concentration assemblies, affects the ink jet printing process. As the ink concentration varies, the optimal parameters used to control the ink jet printing process change as a function of the ink concentration.

In a continuous ink jet fluid system, the ink used, which includes a carrier fluid, such as water or a solvent, and dye, is continuously recirculated through the system under vacuum and mixed with air. Evaporation of the carrier fluid due to the air-ink interaction increases the dye concentration of the ink.

Proper dye concentration is essential to the operation of an ink jet print head. The measurement of dye concentration is used to determine the amount of replenisher needed to mix with the ink to compensate for the carrier fluid lost due to evaporation. When printing rates are high, the amount of dye and carrier fluid removed from the system are typically approximately equal and the ink concentration is maintained, thus, only ink is added to the system.

Alternatively, when little or no printing is being done, the system is in an idle condition and the evaporation rate of the carrier fluid is typically higher than the amount of dye removed during printing. In this instance, then, the dye concentration level increases. A replenishment fluid is needed to bring the ink concentration level down to the proper mixture since high ink concentration affects properties of the ink which are critical to the functions of an ink jet print head. As would be obvious to one skilled in the art, affecting ink properties such as viscosity is detrimental, since the energy required to stimulate filaments is determined partially by the viscosity of the fluid.

Maintaining ink concentration in a continuous ink jet printing system is known in the art. In such a system, ink is passed through a manufactured cell that has a gap of approximately 0.1 mm. An LED light source is used to pass light through the gap and two collectors receive the light. One collector is located so as to receive the light directly to be used as a reference, while the other collector is located on the opposite side of the cell and measures the amount of light transmitted through the cell. As the concentration of the ink in the fluid system increases, the light transmitted through the cell decreases, allowing for a measurable difference. This measurable difference can be used to determine the amount of replenisher fluid needed to replace lost fluid in the system. A device for measuring this difference is an optical concentration apparatus (OCA).

Unfortunately, the OCA is limited by the operating wavelength of the LED light source and by the gap of the manufactured cell. Additionally, the operation of the OCA is restricted to solvent based inks that transmit sufficient light in the visible spectrum with the given gap of 0.1 mm in the manufactured cell. Solvent and water based inks with high absorption in the visible spectrum will not operate with an OCA, making the currently used, commercially available cells both expensive and incapable of use with all ink types.

It is seen then that there exists a need for an ink concentration measuring circuit which overcomes the restrictions typically imposed by use of an OCA.

SUMMARY OF THE INVENTION

This need is met by the system according to the present invention, wherein an optical device capable of maintaining ink concentration at a low cost for an ink jet printing system can use all carrier based, including both solvent and water, inks.

In accordance with one aspect of the present invention, an ink concentration sensor is used with an ink jet printer. The ink concentration sensor comprises a transparent fluid chamber and an infrared light source for directing a beam of IR light at the fluid chamber. A first sensor is located for receiving IR light reflected from the surface of the chamber and providing a reference signal and a second sensor is located for receiving IR light transmitted through the chamber to produce a concentration signal. A circuit means receives the reference signal and generates a corrected concentration signal.

Accordingly, it is an object of the present invention to provide an ink concentration sensor for use with an ink jet printing system which is capable of using all carrier based inks, including solvent and water.

Other objects and advantages of the invention will be apparent from the following description, the accompanying drawings and the appended claims.

BRIEF DESCRIPTION OF THE DRAWINGS

FIG. 4 is a block diagram of the ink concentration sensor of the present invention.

DETAILED DESCRIPTION OF THE PREFERRED EMBODIMENTS

The present invention senses and maintains ink concentration for an ink jet printing system using any carrier based ink. If the ink concentration is too high, a dilutant may be added to dilute the fluid in the ink cell. Alternatively, if the ink concentration is too low, ink may be added to the fluid.

Figure 1:
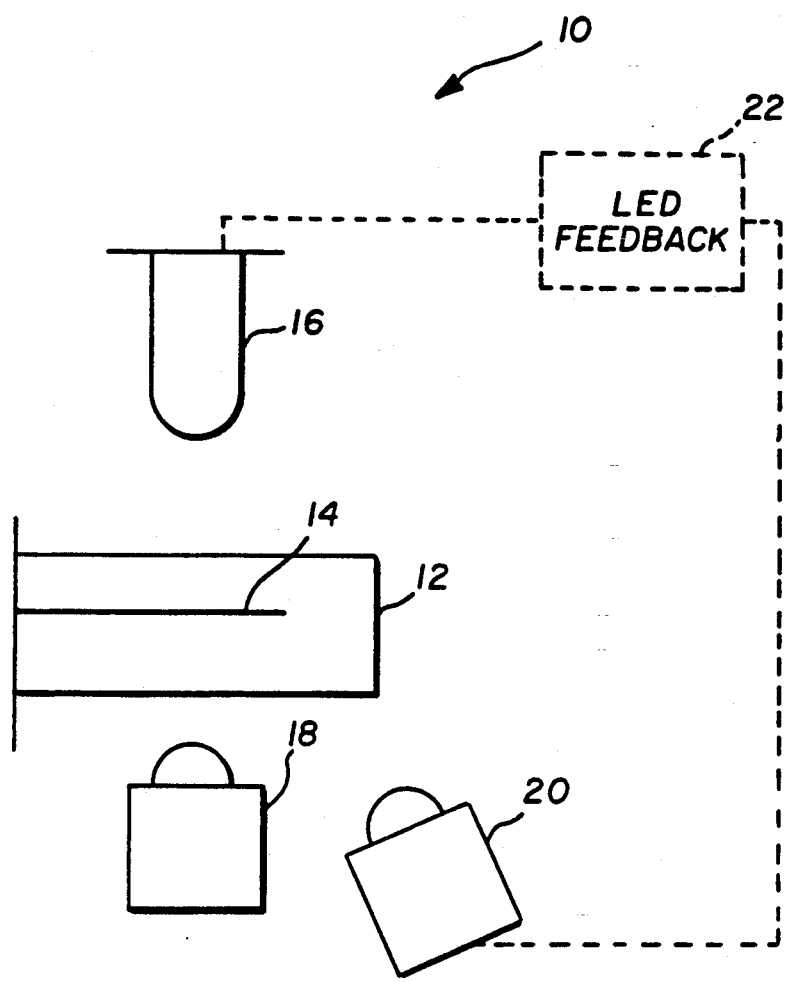
FIG. 1 is a block diagram of a prior art ink concentration measuring circuit.

Referring now to the drawings, in FIG. 1 a prior art optical concentration assembly (OCA) 10 is illustrated. The OCA 10 includes any suitable commercially available ink cell 12 having an ink concentration and having a gap 14 of approximately 0.1 mm. In the OCA 10, light is emitted from a light source 16 operating at 650 nanometers toward the ink cell 12. A first collector diode 18 receives light through the cell gap 14 and a second collector diode 20 receives light through direct transmission of the light source 16. The measurement of direct light received by the second collector diode 20 is provided to a light source feedback 22, which provides the information to the light source 16. Since, obviously, the ink concentration in the ink cell 12 affects the amount of light that is directed through the ink cell 12 to the second collector diode 20, the light source feedback provides an indication of the ink concentration in the ink cell 12.

Figure 2:
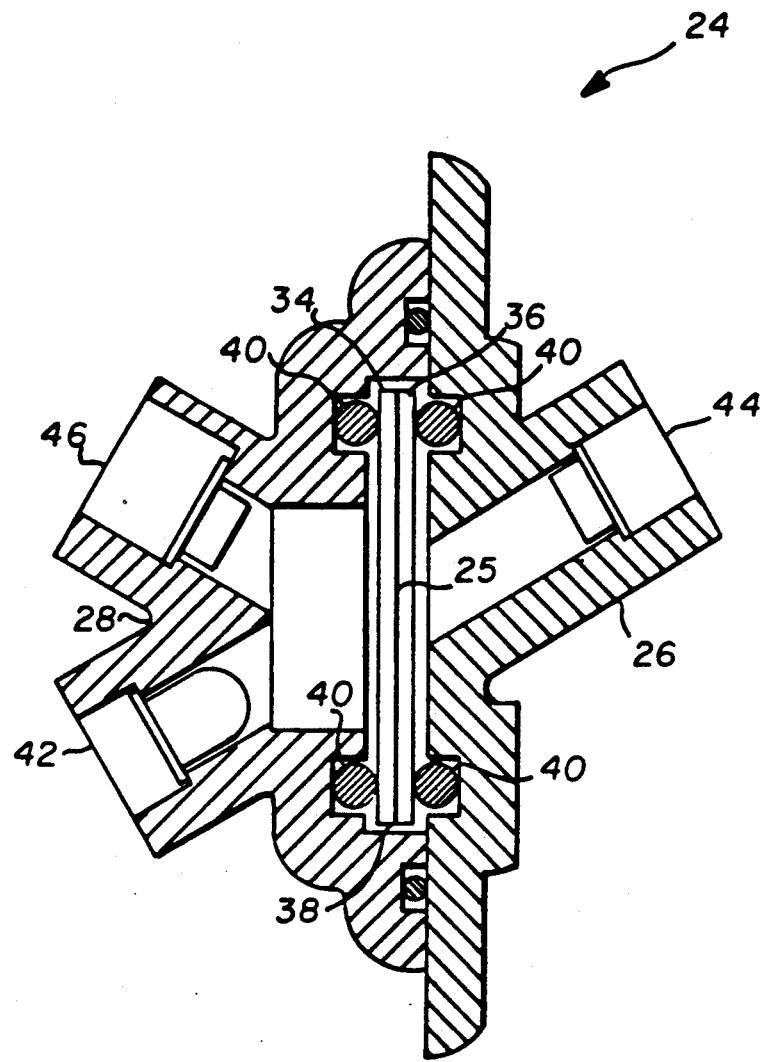
FIG. 2 is a cutaway side view of an ink concentration sensor of the present invention.

Referring now to FIG. 2, an ink concentration sensor 24 of the present invention is illustrated. The present invention uses a light source 42, such as an LED, having an operating wavelength of approximately 870 nm that enables the device 24 to be used with all carrier based inks, solvent or water. It is seen, then, that the present invention eliminates the need for a manufactured cell which is expensive and only offers particular cell gaps.

Figure 3:
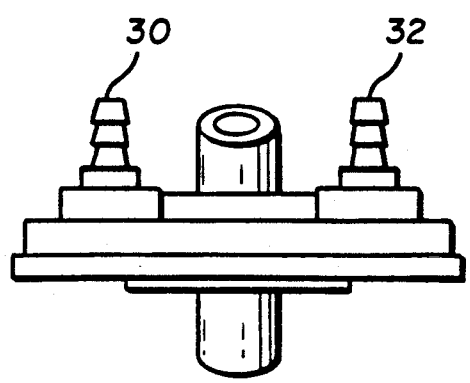
FIG. 3 is a side view of an ink concentration sensor of the present invention.

In FIG. 2, the ink concentration sensor 24 is used for ink concentration control. The sensor 24 includes a transparent fluid chamber 25 and a housing means having first and second housing portions 26 and 28 which define a fluid inlet 30 and a fluid outlet 32, both shown in FIG. 3, and a fluid flow path from the inlet 30 to the outlet 32. Ink is passed from the inlet 30 to the outlet 32 between a pair of transparent glass slides 34 and 36 that have a fixed gap of preferably approximately 0.38 mm. The gap is fixed by a spacer means 38, such as a stainless steel shim. A plurality of o-rings 40 can be used to provide a leak-tight seal between the pair of glass slides 34 and 36 and the housing portions 26 and 28, and can establish the ink flow path.

Continuing with FIG. 2, the infrared light source 42, typically at 870 nm, directs a beam of IR light at the fluid chamber 25. Light is transmitted through the ink path and, by reflection, to a first and second sensor 44 and 46, respectively. The sensors 44 and 46 are preferably identical photodiodes or collectors. The second sensor 46 receives reflected light and is used as a reference.

Continuing with FIG. 2 and referring also to FIG. 4, ink concentration sensor 24 also includes a circuit means 48 which receives the reference signal from the second sensor 46 and generates a corrected concentration signal 50. The output of the second sensor 46, then, is compared to the output of the first sensor 44 that receives light through the ink path. The outputs of the first and second sensors 44 and 46 are divided and compared, using any suitable comparison means and compensation means indicated by block 52 such as a computer, to achieve compensation for temperature and light degradation of the light source 42. Additionally, the first and second sensors 44 and 46 may also be pulsed by a pulsing means of a signal receiving means 54 to the frequency of the light source 42 to minimize noise generated from ambient light and electrical noise in the circuit.

The ink concentration sensor 24 may be calibrated by a calibration means of the signal receiving means 54 by passing calibration fluid through the gap and setting the output of the sensors 44 and 46 to a switch point controllable through a computer. The switch point is determined by the ratio of the output of the signal photodiode 44 to the reference photodiode 46. When the ink concentration in the ink jet printer system increases, the output ratio of the signal photodiode and the reference photodiode falls below the level of the switch point. In this situation, then, the ink jet printer system will fill with replenishment fluid to bring the level of the ink concentration down.

Industrial Applicability and Advantages

The present invention is useful in the field of ink jet printing, and has the advantage of sensing ink concentration. The present invention provides the further advantage of maintaining ink concentration for all types of inks used in ink jet fluid systems. Finally, the ink concentration sensor of the present invention provides the advantage of incorporating a low cost design for ink concentration sensing and control.

Having described the invention in detail and by reference to the preferred embodiment thereof, it will be apparent that other modifications and variations are possible without departing from the scope of the invention defined in the appended claims.

What is claimed is:

1. An ink concentration sensor for use in an ink jet printer, comprising:
   a. a transparent fluid chamber having a pair of transparent glass plates and spacer means for separating the pair of glass plates by a predetermined amount;
   b. an infrared light source for directing a beam of IR light at said fluid chamber;
   c. a first sensor located for receiving IR light transmitted through the chamber to provide an ink concentration signal;
   d. a second sensor located for receiving IR light reflected from the surface of the chamber and providing a reference signal; and
   e. circuit means for receiving the reference signal and generating a corrected ink concentration signal.

2. The ink concentration sensor as claimed in claim 1, wherein the fluid chamber further comprises housing means including a first and second manifold defining a fluid inlet and a fluid outlet and a fluid flow path from the inlet to the outlet between the glass plates.

3. The ink concentration sensor as claimed in claim 2, wherein the second housing portion further comprises support for the infrared light source and the first and second sensors.

4. The ink concentration sensor as claimed in claim 1, wherein the first and second sensors comprise identical photodiodes.

5. The ink concentration sensor as claimed claim 1, further comprising comparison means for comparing the reference signal of the second sensor to the ink concentration signal of the first sensor.

6. The ink concentration sensor as claimed in claim 5, wherein the comparison means comprises a computer.

7. The ink concentration sensor as claimed in claim 1, further comprising compensation means for compensating for temperature and light degradation of the infrared light source.

8. The ink concentration sensor as claimed claim 1, further comprising means for pulsing the first and second sensors to a frequency of the light source to minimize noise generated from ambient light and electrical noise in the circuit.

9. The ink concentration sensor as claimed in claim 2 further comprising calibration means for calibrating the ink concentration sensor.

10. The ink concentration sensor as claimed in claim 9 wherein the calibration means comprises means for passing calibration fluid through a gap fixed by the spacer means.

* * * * *